(12) United States Patent
Jones et al.

(10) Patent No.: US 6,190,899 B1
(45) Date of Patent: Feb. 20, 2001

(54) CELLULASE PRODUCING ACTINOMYCETES, CELLULASE PRODUCED THEREFROM AND METHOD OF PRODUCING SAME

(75) Inventors: Brian E. Jones, Leidschendam; Wilhelmus A. H. Van Der Kleij, Naaldwijk; Piet Van Solingen, Naaldwijk, all of (NL); Walter Weyler, San Francisco, CA (US)

(73) Assignee: Genencor International, Inc., Rochester, NY (US)

( * ) Notice: Under 35 U.S.C. 154(b), the term of this patent shall be extended for 0 days.

(21) Appl. No.: 09/102,204

(22) Filed: Jun. 22, 1998

Related U.S. Application Data

(63) Continuation-in-part of application No. 08/974,041, filed on Nov. 19, 1997, now abandoned.

(51) Int. Cl.$^7$ .............................. C12N 9/42; C11D 3/386
(52) U.S. Cl. ........................ 435/209; 435/263; 510/392
(58) Field of Search .................................. 435/209, 263; 510/392

(56) References Cited

U.S. PATENT DOCUMENTS

| | | | |
|---|---|---|---|
| 5,792,641 | 8/1998 | Schulein et al. ...................... | 435/209 |
| 5,871,550 | 2/1999 | Goedegebuur et al. ................. | 8/137 |

FOREIGN PATENT DOCUMENTS

| | | |
|---|---|---|
| 61-012282 | 1/1986 | (JP) . |
| WO 96/00281 | 1/1996 | (WO) . |
| WO 96/34092 | 10/1996 | (WO) . |
| WO 96/34108 | 10/1996 | (WO) . |
| WO 97/27363 | 7/1997 | (WO) . |

OTHER PUBLICATIONS

Wilson, D.B. (1992) Crit. Rev. Biotechnol. 12(1/2), 45–63.

Lao, G. et al, "DNA sequences of three beta–1, 4 endoglucanase genes from *Thermomonospora fusca*" Journal of Bacteriology, vol. 173, No. 11, pp. 3397–3407 (1991).

Theberge M. et al, "Purification and characterization of an endoglucanase from *Streptomyces livdans* 66 and DNA sequence of the gene", *Applied and Environmental Biology*, vol. 58, No. 3, pp. 815–820, (1992).

Nakai, R. et al., "Cloning and nucleotide sequence of a cellulase gene cas–A from Alkalophilic Streptomyces strain", *Gene*, vol. 65, No. 2, pp. 229–238 (1998).

Nakai, R. et al, "Purification and properties of cellulases from an alkalophilic Streptomyces strain", *Agricultural and Biological Chemistry*, vol. 51, No. 11, pp. 3061–3065, (1987).

Garda. A.L. et al., "Two genes encoding an endoglucanase and a cellulose binding protein are clustered and co–regulated by a TTA codon in *Streptomyces halstedii* JM8", Biochem. J. vol. 324, pp. 403–411, (1997).

Perito, B. et al., "characterization and sequence analysis of a *Streptomyces rochei* A2", Gene vol. 148, pp. 119–124 (1994).

Wittman, S., et al., "Purification and characterization of the CelB endoglucanase from *Streptomyces lividans* 66 and DNA sequence of the encoding gene". App. and Environ. Microbiol., vol. 60, No. 5, pp. 1701–1703 (1994).

Shikata, S., et al., "Alkaline cellulases for Laundry detergents: production by alkalophilic strains of Bacillus and some properties of the crude enzymes", Ag. And Biol. Chem. vol. 54, No. 1, pp. 91–96 (1990).

*Primary Examiner*—Charles L. Patterson, Jr.
(74) *Attorney, Agent, or Firm*—Susan K. Faris; Lynn Marcus-Wyner

(57) ABSTRACT

A novel cellulase composition is provided which is producible by an Actinomycete. The cellulase has an approximate calculated molecular weight of 35 kD and has a pH optimum at 40° C. of 6 and at 60° C. of 6 or less. Also provided is a DNA encoding said cellulase, a method for producing the cellulase and applications thereof.

16 Claims, 4 Drawing Sheets

```
Met Ile Ser Ser His Gly Arg His Arg Arg Ser Leu Arg Thr Arg
 1           5                  10                 15
Leu Leu Ala Pro Leu Ala Gly Leu Leu Ala Ala Gly Gly Leu Met Ala
         20                  25              30
Ala Gly Thr Leu Ala Ala Ala Gly Thr Gly Asp Gln Ala Pro Gln Ala
         35                  40              45
Leu Thr Pro Phe Gln Glu His Gly Arg Leu Glu Val Cys Gly Thr Arg
     50              55              60
Leu Cys Asp Glu Asn Gly Glu Val Gln Leu Arg Gly Met Ser Thr
 65              70              75              80
His Gly Thr Gln Trp Tyr Ala His Cys Val Thr Glu Gly Ser Leu Asp
             85              90              95
Ala Leu Ala Gly Asp Trp Gly Ala Asp Val Leu Arg Val Ser Thr Tyr
         100             105             110
Val Gln Glu Gly Gly Tyr Glu Thr Asp Pro Glu Arg Phe Thr Asp Ile
         115             120             125
Ala Gly Arg Ile Ile Asp Gln Ala Thr Glu Arg Gly Leu Tyr Val Val
         130             135             140
Val Asp Trp His Gln Leu Ser Pro Gly Asp Pro Asn His Asn Thr Glu
145             150             155             160
Arg Ala Lys Arg Phe Phe Arg Asp Ile Thr Ala Arg His Gly His Gln
             165             170             175
Asp Asn Leu Leu Tyr Glu Ile Ala Asn Glu Pro Asn Gly Val Gly Trp
         180             185             190
Gln Ala Ile Lys Asn Tyr Ala Glu Glu Val Ile Pro Val Val Arg Ala
         195             200             205
Gly Asp Pro Asp Ala Val Val Leu Val Gly Thr Arg Ala Trp Ser Ser
     210             215             220
Leu Gly Val Ser Glu Gly Ser Asp Glu Arg Glu Ile Leu Ala Asp Pro
225             230             235             240
Val Asp Ala Asp Asn Ile Met Tyr Thr Phe His Phe Tyr Ala Ala Ser
             245             250             255
His Arg Glu Pro Tyr Leu Glu Thr Leu Ser Arg Ala Ala Asp Ser Ile
             260             265             270
Pro Val Phe Val Thr Glu Phe Gly Thr Gln Asp Tyr Ser Gly Glu Gly
         275             280             285
Ala Asn Asp Phe Ser Met Ala Gln Arg Tyr Leu Asp Leu Met Ala Glu
     290             295             300
Lys Lys Ile Ser Trp Ile Asn Trp Asn Phe Ser Asp Asp Trp Arg Ser
305             310             315             320
Gly Ala Val Phe Arg Glu Gly Thr Cys Ser Gly Asp Arg Trp Thr Gly
             325             330             335
Thr Gly Val Leu Lys Glu Ala Gly Val Trp Ile Arg Glu Arg Ile Gly
         340             345             350
```

```
ATGATCTCAT CGCACGGTCG GCACCGGCGG CGCTCCCTCC GCACCCAGGTT GCTGGCCCCG    60
CTGGCCGGGC TCCTGGCGGC CGGCGGACTG ATGGCGGGCG GGACGCTCGC CGCGGCCCGC   120
ACCGGCGACC AGGCCCCGCA GGCTCTCACC CCGTTCCAGG AGCACGGCCG TCTGGAGGTC   180
TGCGGCACCC GCCTGTGCGA CGAGAACGGC GAGGAGGTGC AGTTGCGGGG CATGAGCACC   240
CACGGCACCC AGTGGTACGC CCACTGCGTC ACCGAGGGGT CGCTCGACGC GCTGGCCGGC   300
GACTGGGGAG CCGACGTCCT GCGGGTGTCC ACCTACGTCC AGGAGGGCGG CTACGAGACC   360
GACCCCGAGC GCTTCACCGA CGCATCATCG CGCATCATCG TCCCCGGGGG ACCAGGCCAC   420
CTGTACGTCG TCGTCGACTG GCACCAGTC TCCCCGGGGG GCGCGCCACG CAACACCGAG   480
CGCGCCAAGC GGTTCTTCCG GACATCACC GCGCTGGCAAG CGATCAAGAA CAACCTGCTG   540
TACGAGATCG CCAACGAACC CAACGGAGTC GGCTGGCAAG CGATCAAGAA CTACGCGGAG   600
GAGGTCATCC CCGTCGTCCG GGCCGGTGAC CCCGACGCGG TCGTCCTGGT CGGCACCCGC   660
GCCTGGTCCT CGCTGGGCGT CTCCGAGGGC AGCGACGAGC GGGAGATCCT GGCCGACCCG   720
GTCGATGCGG ACAACATCAT GTACACCTTC CACTTCTACG CCGCCTCGCA CCGCGAGCCC   780
TACCTGGAGA CGCTCTCCCG GGCCGCGAAC AGCATCCCCG TGTTCGTCAC CGAGTTCGGC   840
ACCCAGGACT ACTCGGGTGA GGGTGCGAAC GACTTCTCCA TGGCCCAGCG CTACCTGGAC   900
CTGATGGCCG AGAAGAAGAT CAGCTGGATC AACTGGAACT TCTCCGACGA CTGGCGCTCG   960
GGCGCGGTGT TCCGCGAGGG CACCTGCTCC GGTGACCGGT GGACGGGCAC CGGCGTGCTC  1020
AAGGAGGCGG GGGTCTGGAT CCGCGAGCGG ATCGGCTGA                         1059
```

FIG._6

```
GATCCTGGCT CAGGACGAAC GCTGGCGGCG TGCTTAACAC ATGCAAGTCG AACGATGAAG    60
CCGCTTCGGT GGTGGATTAG TGGCGAACGG GTGAGTAACA CGTGGGCAAT CTGCCCTGCA   120
CTCTGGGACA AGCCCGGGAA ACTGGGTCTA ATACCGGATA -TGACACACG ACCGCATGGT   180
CTGTGTGTGG AAAGCTCCGG CGGTGCAGGA TGAGCCCGCG GCCTATCAGC TTGTTGGTGG   240
GGTAATGGCC TACCAAGGCG ACGACGGGTA CCCGGCCTGA GAGGGCGACC GGCCACACTG   300
GGACTGAGAC ACGGCCCAGA CTCCTACGGG AGGCAGCAGT GGGGAATATT GCACAATGGG   360
CGAAAGCCTG ATGCAGCGAC GCCGCGTGAG GGATGACGGC CTTCGGGTTG TAAACCTCTT   420
TCA                                                                421
```

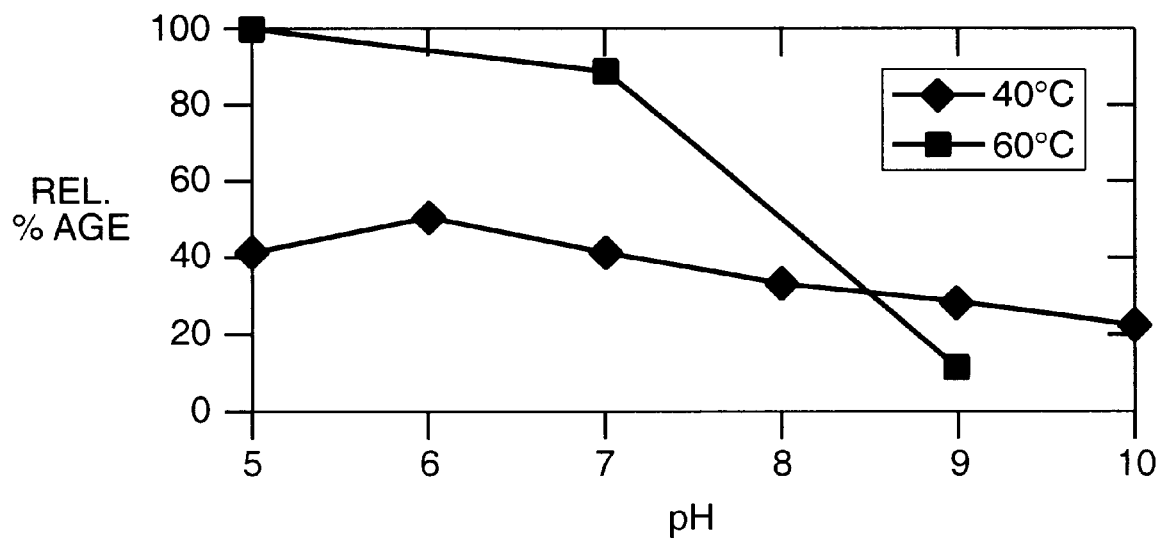
FIG._3

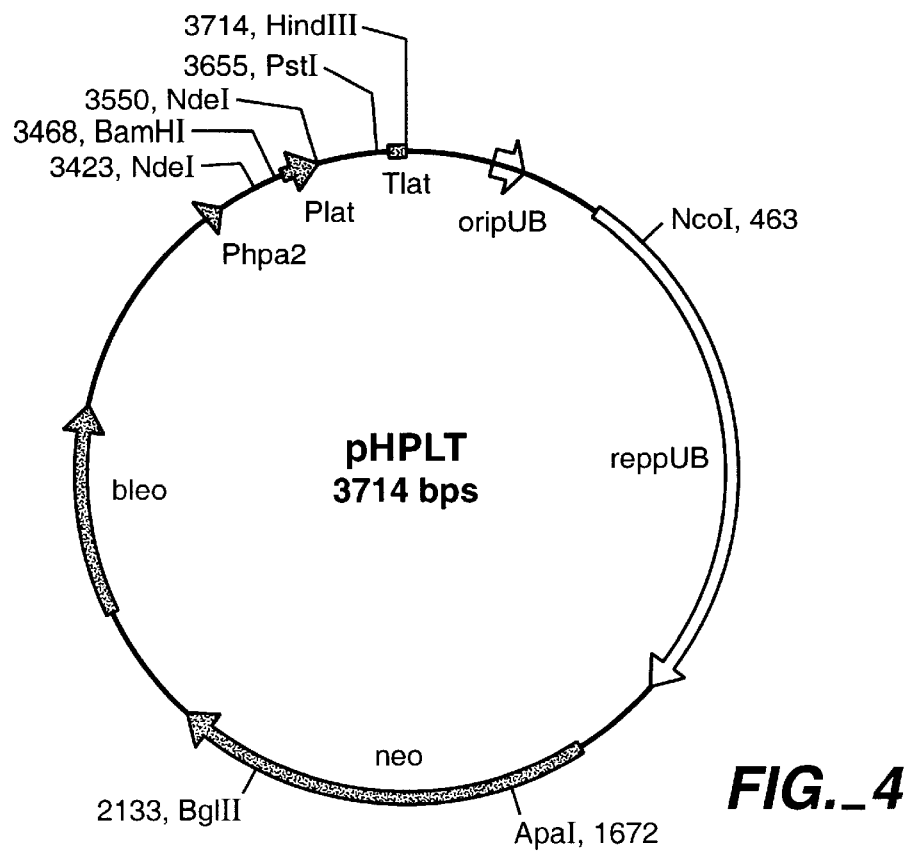
FIG._4
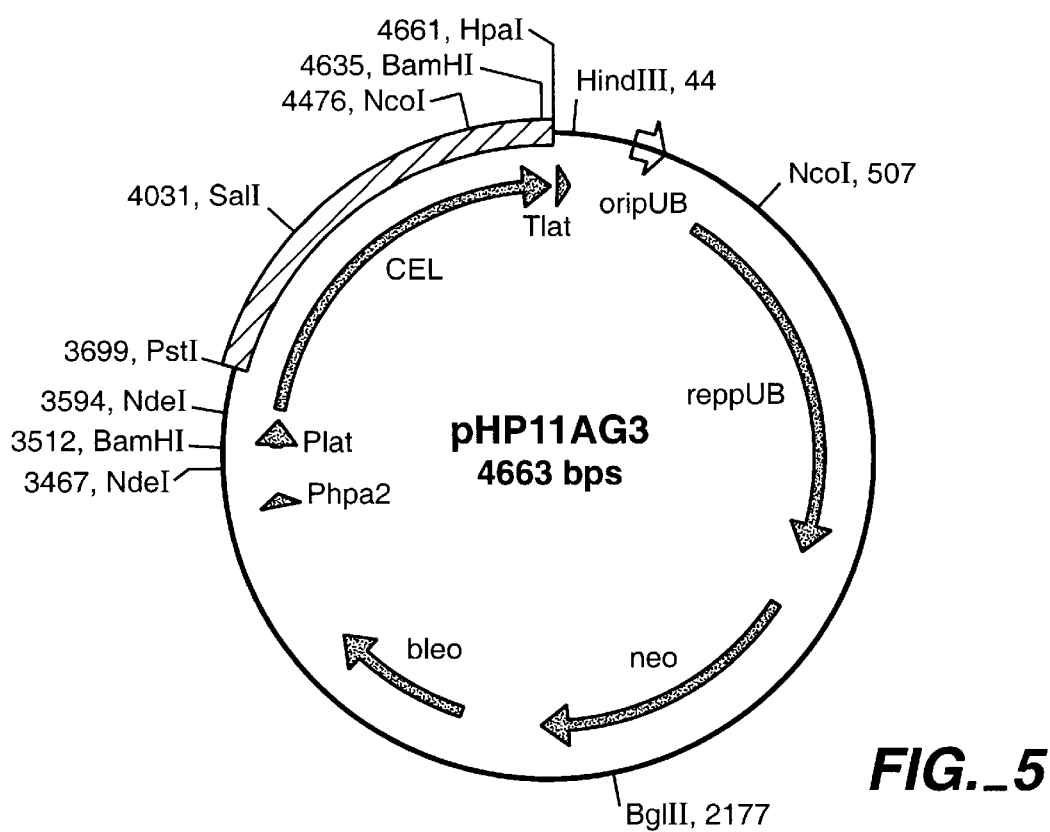
FIG._5

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 352 amino acids
        (B) TYPE: amino acid
        (C) STRANDEDNESS: single
        (D) TOPOLOGY: linear (xi) SEQUENCE DESCRIPTION: SEQ ID NO:1:

```
Met Ile Ser Ser His Gly Arg His Arg Arg Ser Leu Arg Thr Arg
  1               5                  10                  15

Leu Leu Ala Pro Leu Ala Gly Leu Leu Ala Ala Gly Gly Leu Met Ala
                 20                  25                  30

Ala Gly Thr Leu Ala Ala Ala Gly Thr Gly Asp Gln Ala Pro Gln Ala
             35                  40                  45

Leu Thr Pro Phe Gln Glu His Gly Arg Leu Glu Val Cys Gly Thr Arg
 50                  55                  60
```

```
Leu Cys Asp Glu Asn Gly Glu Glu Val Gln Leu Arg Gly Met Ser Thr
 65                  70                  75                  80

His Gly Thr Gln Trp Tyr Ala His Cys Val Thr Glu Gly Ser Leu Asp
                 85                  90                  95

Ala Leu Ala Gly Asp Trp Gly Ala Asp Val Leu Arg Val Ser Thr Tyr
            100                 105                 110

Val Gln Glu Gly Gly Tyr Glu Thr Asp Pro Glu Arg Phe Thr Asp Ile
        115                 120                 125

Ala Gly Arg Ile Ile Asp Gln Ala Thr Glu Arg Gly Leu Tyr Val Val
    130                 135                 140

Val Asp Trp His Gln Leu Ser Pro Gly Asp Pro Asn His Asn Thr Glu
145                 150                 155                 160

Arg Ala Lys Arg Phe Phe Arg Asp Ile Thr Ala Arg His Gly His Gln
                165                 170                 175

Asp Asn Leu Leu Tyr Glu Ile Ala Asn Glu Pro Asn Gly Val Gly Trp
            180                 185                 190

Gln Ala Ile Lys Asn Tyr Ala Glu Glu Val Ile Pro Val Val Arg Ala
        195                 200                 205

Gly Asp Pro Asp Ala Val Val Leu Val Gly Thr Arg Ala Trp Ser Ser
    210                 215                 220

Leu Gly Val Ser Glu Gly Ser Asp Glu Arg Glu Ile Leu Ala Asp Pro
225                 230                 235                 240

Val Asp Ala Asp Asn Ile Met Tyr Thr Phe His Phe Tyr Ala Ala Ser
                245                 250                 255

His Arg Glu Pro Tyr Leu Glu Thr Leu Ser Arg Ala Ala Asp Ser Ile
            260                 265                 270

Pro Val Phe Val Thr Glu Phe Gly Thr Gln Asp Tyr Ser Gly Glu Gly
        275                 280                 285

Ala Asn Asp Phe Ser Met Ala Gln Arg Tyr Leu Asp Leu Met Ala Glu
    290                 295                 300

Lys Lys Ile Ser Trp Ile Asn Trp Asn Phe Ser Asp Asp Trp Arg Ser
305                 310                 315                 320

Gly Ala Val Phe Arg Glu Gly Thr Cys Ser Gly Asp Arg Trp Thr Gly
                325                 330                 335

Thr Gly Val Leu Lys Glu Ala Gly Val Trp Ile Arg Glu Arg Ile Gly
            340                 345                 350

(2) INFORMATION FOR SEQ ID NO:2:

(i) SEQUENCE CHARACTERISTICS:
        (A) LENGTH: 1059 base pairs
        (B) TYPE: nucleic acid
        (C) STRANDEDNESS: single
        (D) TOPOLOGY: linear (xi) SEQUENCE DESCRIPTION: SEQ ID NO:2:

ATGATCTCAT CGCACGGTCG GCACCGGCGG CGCTCCCTCC GCACCAGGTT GCTGGCCCCG     60

CTGGCCGGGC TCCTGGCGGC CGGCGGACTG ATGGCGGCGG GGACGCTCGC CGCGGCCGGC    120

ACCGGCGACC AGGCCCCGCA GGCTCTCACC CCGTTCCAGG AGCACGGCCG TCTGGAGGTC    180

TGCGGCACCC GCCTGTGCGA CGAGAACGGC GAGGAGGTGC AGTTGCGGGG CATGAGCACC    240

CACGGCACCC AGTGGTACGC CCACTGCGTC ACCGAGGGGT CGCTCGACGC GCTGGCCGGC    300

GACTGGGGAG CCGACGTCCT GCGGGTGTCC ACCTACGTCC AGGAGGGCGG CTACGAGACC    360

GACCCCGAGC GCTTCACCGA CATCGCCGGC CGCATCATCG ACCAGGCCAC CGAGCGCGGC    420
```

-continued

```
CTGTACGTCG TCGTCGACTG GCACCAGCTC TCCCCGGGGG ACCCGAACCA CAACACCGAG      480

CGCGCCAAGC GGTTCTTCCG GGACATCACC GCGCGCCACG GCCACCAGGA CAACCTGCTG      540

TACGAGATCG CCAACGAACC CAACGGAGTC GGCTGGCAAG CGATCAAGAA CTACGCGGAG      600

GAGGTCATCC CCGTCGTCCG GGCCGGTGAC CCCGACGCGG TCGTCCTGGT CGGCACCCGC      660

GCCTGGTCCT CGCTGGGCGT CTCCGAGGGC AGCGACGAGC GGGAGATCCT GGCCGACCCG      720

GTCGATGCGG ACAACATCAT GTACACCTTC CACTTCTACG CCGCCTCGCA CCGCGAGCCC      780

TACCTGGAGA CGCTCTCCCG GGCCGCCGAC AGCATCCCGG TGTTCGTCAC CGAGTTCGGC      840

ACCCAGGACT ACTCGGGTGA GGGTGCGAAC GACTTCTCCA TGGCCCAGCG CTACCTGGAC      900

CTGATGGCCG AGAAGAAGAT CAGCTGGATC AACTGGAACT TCTCCGACGA CTGGCGCTCG      960

GGCGCGGTGT TCCGCGAGGG CACCTGCTCC GGTGACCGGT GGACGGGCAC CGGCGTGCTC     1020

AAGGAGGCGG GGGTCTGGAT CCGCGAGCGG ATCGGCTGA                            1059

(2) INFORMATION FOR SEQ ID NO:3:

(i) SEQUENCE CHARACTERISTICS:
        (A) LENGTH: 421 base pairs
        (B) TYPE: nucleic acid
        (C) STRANDEDNESS: single
        (D) TOPOLOGY: linear (xi) SEQUENCE DESCRIPTION: SEQ ID NO:3:

GATCCTGGCT CAGGACGAAC GCTGGCGGCG TGCTTAACAC ATGCAAGTCG AACGATGAAG       60

CCGCTTCGGT GGTGGATTAG TGGCGAACGG GTGAGTAACA CGTGGGCAAT CTGCCCTGCA      120

CTCTGGGACA AGCCCGGGAA ACTGGGTCTA ATACCGGATA TGACACACGA CCGCATGGTC      180

TGTGTGTGAA AGCTCCGGCG GTGCAGGATG AGCCCGCGGC CTATCAGCTT GTTGGTGGGG      240

TAATGGCCTA CCAAGGCGAC GACGGGTAGC CGGCCTGAGA GGGCGACCGG CCACACTGGG      300

ACTGAGACAC GGCCCAGACT CCTACGGGAG GCAGCAGTGG GGAATATTGC ACAATGGGCG      360

AAAGCCTGAT GCAGCGACGC CGCGTGAGGG ATGACGGCCT TCGGGTTGTA AACCTCTTTC      420

A                                                                     421
```

CELLULASE PRODUCING ACTINOMYCETES, CELLULASE PRODUCED THEREFROM AND METHOD OF PRODUCING SAME

CROSS-REFERENCE TO RELATED APPLICATIONS

This application is a continuation-in-part of U.S. application Ser. No. 08/974,041, filed Nov. 19, 1997, now abandoned and which is incorporated herein by reference in its entirety.

BACKGROUND OF THE INVENTION

A. Technical Field

The present invention relates to cellulase compositions produced by Actinomycete, methods of producing such cellulases and the use of such cellulases. The present invention further relates to the use of the novel cellulase in compositions recognized in the art as advantageously having cellulase added thereto, including, as an additive in a detergent composition, in the treatment of textiles such as cellulose containing fabrics and fibers useful therefor, as an animal feed additive, as a processing aid in baking, in the treatment of pulp and paper and in the treatment of starch for the production of high fructose corn-syrup or ethanol.

B. State of the Art

Cellulases are enzymes which are capable of the hydrolysis of the β-D-glucosidic linkages in celluloses. Cellulolytic enzymes have been traditionally divided into three major classes: endoglucanases, exoglucanases or cellobiohydrolases and β-glucosidases (Knowles, J. et al., (1987), *TIBTECH* 5, 255–261); and are known to be produced by a large number of bacteria, yeasts and fungi.

Primary among the applications that have been developed for the use of cellulolytic enzymes are those involving degrading (wood) cellulose pulp into sugars for (bio)ethanol production, textile treatments like 'stone washing' and 'biopolishing', and in detergent compositions. Thus, cellulases are known to be useful in detergent compositions for removing dirt, i.e., cleaning. For example, Great Britain Application Nos. 2,075,028, 2,095,275 and 2,094,826 illustrate improved cleaning performance when detergents incorporate cellulase. Additionally, Great Britain Application No. 1,358,599 illustrates the use of cellulase in detergents to reduce the harshness of cotton containing fabrics.

Another useful feature of cellulases in the treatment of textiles is their ability to recondition used fabrics by making their colors more vibrant. For example, repeated washing of cotton containing fabrics results in a greyish cast to the fabric which is believed to be due to disrupted and disordered fibrils, sometimes called "pills", caused by mechanical action. This greyish cast is particularly noticeable on colored fabrics. As a consequence, the ability of cellulase to remove the disordered top layer of the fiber and thus improve the overall appearance of the fabric has been of value.

Because detergents, being a primary application of cellulase, operate generally under alkaline conditions there is a strong demand for cellulases which have excellent activity at pH 7–10. Well characterized fungal cellulases, such as those from *Humicola insolens* and *Trichoderma reesei*, perform adequately at neutral to low alkaline pH. Further, a number of enzymes that show cellulase activity at high alkaline pH have been isolated from Bacillus and other prokaryotes, see e.g., PCT Publication Nos. WO 96/34092 and WO 96/34108. Thus, both fungal and bacterial cellulases have been investigated thoroughly. However, a third group of cellulases, those isolated from Actinomycetes, have attracted only some attention. Wilson et al., *Critical Reviews in Biotechnology*, Vol. 12, pp. 45–63 (1992), studied the cellulases produced by the *Thermomonospora fusca, Thermonomospora curvata* and *Microbispora bispora* and illustrated that many of these cellulases show broad pH profiles and good temperature stability. Similarly, Nakai et al.,*Agric. Biol. Chem.,* Vol. 51, pp. 3061–3065 (1987) and Nakai et al., *Gene*, Vol. 65, pp. 229–238 (1988) exemplify the alkalitolerant cellulase casA from Streptomyces strain KSM-9 which also possesses an alkaline pH optimum and excellent temperature stability.

Despite knowledge in the art related to many cellulase compositions having desirable properties, including those from Actinomycetes, there is a continued need for new cellulases having a varying spectrum of characteristics which are useful in, for example, treating textiles, as a component of detergent compositions, in the treatment of pulp and paper, as an animal feed supplement, as a processing aid for baking and in the conversion of biomass. Applicants have discovered certain cellulases which have such a complement of characteristics and which are useful in such known applications of cellulase.

SUMMARY OF THE INVENTION

It is an object of the present invention to provide for novel Actinomycete derived cellulase compositions having useful temperature and pH profiles for use in detergents.

It is a further object of the present invention to provide for novel Actinomycete derived cellulase compositions having useful characteristics for the treatment of textiles so as to produce desirable qualities in textile yarns, fabrics and garments.

It is a further object of the present invention to provide for novel Actinomycete derived cellulases which have useful characteristics for use as an animal feed additive, as a baking aid, in the treatment of pulp and paper and in the reduction of biomass.

It is a further object of the present invention to provide for a method of producing cellulase compositions derived from such novel Actinomycetes.

It is yet a further object of the present invention to provide a DNA and amino acid sequence which facilitate industrial production of the novel cellulase compositions of the invention.

It is still a further object of the present invention to provide a novel cellulase having excellent properties for use in detergents, treating textiles, as a feed supplement and in pulp and paper manufacturing.

According to the present invention, a novel cellulase is provided which is obtainable from an Actinomycete or a derivative of said cellulase. Preferably, the cellulase of the invention comprises an amino acid sequence according to FIG. 1 (SEQ ID NO: 1), or a derivative thereof having greater than 62% sequence identity, preferably greater than 75% sequence identity and more preferably greater than 90% sequence identity thereto.

According to another embodiment, a composition is provided comprising DNA encoding the cellulase of the invention. Preferably, the DNA encodes an amino acid sequence according to FIG. 2 (SEQ ID NO:2), or a derivative thereof having greater than 72% sequence identity, preferably greater than 80% sequence identity and more preferably greater than 90% sequence identity thereto and cellulases produced thereby. The present invention further embodies DNA which hybridizes to a DNA probe taken from the DNA represented in FIG. 2 under the appropriate conditions and cellulases produced thereby.

According to yet another embodiment of the invention, a method of transforming a suitable microorganism with DNA encoding a cellulase according to the invention is provided and a method of producing the cellulase according to the invention from that transformed microorganism.

In an especially preferred embodiment of the present invention, the mature cellulase is derived from Actinomycete and has a molecular weight of approximately 35 kD as measured on SDS-PAGE (referred to herein as the 35 kD cellulase). The mature approximately 35 kD cellulase has a calculated isoelectric point of about 4.5 and a pH optimum on CMC of about 6 at 40° C. and 6 or less at 60° C. The cellulase of the present invention showed higher activity at 60° C. than at 40° C. with broad activity ranges from at least pH 5 to pH 10.

BRIEF DESCRIPTION OF THE DRAWINGS

FIG. 1 shows the deduced amino acid sequence of an approximately 35 kD cellulase according to the invention showing the leader sequence in bold. Coded letters are according to the IUPAC-IUB Biochemical Nomenclature Commission (as described in the GenBank PatentIn User Manual, PC-DOS/MS-DOS Version, November, 1990) (SEQ. ID. NO:1).

FIG. 2 shows the DNA sequence encoding an approximately 35 kD cellulase according to the invention (SEQ.ID.NO:2).

FIG. 3 shows the pH/activity profile of an approximately 35 kD cellulase according to the invention at 40° C. and 60° C.

FIG. 4 shows the pHPLT vector.

FIG. 5 shows the pHP11AG3 vector.

FIG. 6 shows the 16s RNA sequence of the Actinomycete from which the cellulase of the invention may be obtained (SEQ.ID.NO:3).

DETAILED DESCRIPTION OF THE INVENTION

"Derivative" is intended to indicate a protein which is derived from the native protein by addition of one or more amino acids to either or both the C- and N-terminal end of the native protein, substitution of one or more amino acids at one or a number of different sites in the native amino acid sequence, deletion of one or more amino acids at either or both ends of the native protein or at one or more sites in the amino acid sequence, or insertion of one or more amino acids at one or more sites in the native amino acid sequence. The preparation of an enzyme derivative is preferably achieved by modifying a DNA sequence which encodes for the native protein, transformation of that DNA sequence into a suitable host, and expression of the modified DNA sequence to form the derivative enzyme. The derivative of the invention includes peptides comprising altered amino acid sequences in comparison with a precursor enzyme amino acid sequence (e.g., a wild type or native state enzyme according to the present invention) and which peptides retain a characteristic enzyme nature of the precursor enzyme but which have altered properties in some specific aspect. For example, an altered cellulase may have an increased pH optimum or increased temperature resistance but will retain its characteristic cellulolytic activity.

"Host cell" means a cell which has the capacity to act as a host and expression vehicle for a recombinant DNA vector according to the present invention. In a preferred embodiment according to the present invention, "host cell" means the cells of Bacillus.

"DNA construct" or "DNA vector" means a nucleotide sequence which comprises one or more DNA fragments encoding any of the novel cellulases or cellulase derivatives described above.

In a preferred embodiment, the cellulase of the invention is an approximately 35 kD cellulase (calculated on the basis of amino acid sequence of the mature protein) derived from Actinomycete (referred to herein as the "35 kD Cellulase"). The 35 kD cellulase has a calculated pI for the mature protein of about 4.5 and a pH optimum on carboxymethylcellulose (CMC) at 40° C. of about 6 and at 60° C. of 5 or less.

The gene encoding the amino acid sequence of the 35 kD cellulase was analyzed by comparison with the accessible sequence data in various libraries (GenBank, Swiss-Prot, EMBL and PIR). A search of databases for a comparison of the cellulase encoded by the DNA sequence of the present invention with cellulases encoded by published or known cellulase gene sequences was performed to determine the closed phylogenetic neighbors. The highest amount of homology found was to cellulase E5 derived from *Thermomonospora fusca* and to CelA from *Streptomyces lividans*. The approximately 35 kD cellulase was shown to be 61.2% identical in amino acid sequence to E5 in a 268 residue overlap and 54.9% identical in sequence to CelA in a 244 base pair overlap using the TFastA program as described by Pearson & Lipman, *Proc. Nat. Acad. Sci.*, Vol. 85, pp. 2444–2448 (1988). The TFastA Data Searching Program is commercially available in the Sequence Analysis Software Package Version 6.0 (Genetic Computer Group, Univ. Wisconsin Biotechnology Center, Madison, Wis. 53705). A comparison of the DNA sequences encoding the 35 kD cellulase in DNA encoding E5 and CelA using the TFastA program demonstrated a nucleotide identity of 71.3% identity to DNA encoding E5 in an 1134 base pair overlap and 62.8% identity to DNA encoding CelA with a 1306 base pair overlap.

Thus, the present invention encompasses a cellulase which has an amino acid sequence according to that in FIG. 1 (SEQ ID NO:1) or a derivative thereof having greater than 62% sequence identity, preferably greater than 75% sequence identity and most preferably greater than 90% sequence identity thereto. Similarly, the present invention further encompasses a DNA according to FIG. 2 (SEQ. ID NO:2) or a derivative there of having greater than 72% sequence identity, preferably greater than 80% sequence identity and most preferably greater than 90% sequence identity thereto.

Hybridization is used herein to analyze whether a given fragment or gene corresponds to the cellulase described herein and thus falls within the scope of the present invention. The hybridization assay is essentially as follows: Genomic DNA from a particular target source is fragmented by digestion with a restriction enzyme(s), e.g., EcoR I, Hind III, Bam HI, Cla I, Kpn I, Mlu I, Spe I, Bgl II, Nco I, Xba I, Xho I and Xma I (supplied by New England Biolabs, Inc., Beverly, Mass. and Boehringer Mannheim) according to the manufacturer's instructions. The samples are then electrophoresed through an agarose gel (such as, for example, 0.8% agarose) so that separation of DNA fragments can be visualized by size. The gel may be briefly rinsed in distilled $H_2O$ and subsequently depurinated in an appropriate solution (such as, for example, 0.25 M HCl) with gentle shaking followed by denaturation for 30 minutes with gentle shaking followed by denaturation for 30 minutes (in, for example, 0.4 M NaOH) with gentle shaking. A renaturation step may be included in which the gel is placed in 1.5 M NaCL, IMTris, pH 7.0 with gentle shaking for 30 minutes. The DNA should then be transferred onto an appropriate positively charged membrane, for example the *Maximum Strength Nytran Plus* membrane (Schleicher & Schuell, Keene, N.H.), using a transfer solution (such as, for example, 6XSSC (900 mM NaCl, 90 mM trisodium citrate)). After the transfer is complete, generally at about 2 hours or greater, the membrane is rinsed and air dried at room temperature after using a rinse solution (such as, for example, 2X SSC[2X SSC=300 mM NaCl, 30 mM trisodium citrate]). The membrane should then be prehybridized, (for approximately 2 hours or more) in a suitable prehybridization solution (such as, for example, an aqueous solution containing per 100 mls: 20–50 mls formamide, 25 mls of 20X SSPE (1X SSPE=0.18 M NaCl, 1 mM EDTA, 10 mM $NaH_2PO_4$, pH 7.7), 2.5 mls of 20% SDS, 1 ml of 10 mg/ml sheared herring sperm DNA). As would be known to one of skill in the art, the amount of formamide in the prehybridization solution may be varied depending on the nature of the reaction obtained according to routine methods. Thus, a lower amount of formamide may result in a more complete gel in terms of identifying hybridizing molecules than the same procedure using a larger amount of formamide. On the other hand, a strong hybridization band may be more easily visually identified by using more formamide.

A DNA probe taken from the sequence in FIG. 2 should be isolated by electrophoresis in an agarose gel, the fragment excised from the gel and recovered from the excised agarose. This purified fragment of DNA is then labeled (using, for example, the Megaprime labeling system according to the instructions of the manufacturer to incorporate $P^{32}$ in the DNA (Amersham International plc, Buckinghamshire, England)). The labeled probe is denatured by heating to 95° C. for 5 minutes and immediately added to the prehybridization solution above containing the membrane. The hybridization reaction should proceed for an appropriate time and under appropriate conditions, for example, for 18 hours at 37° C. with gentle shaking. The membrane is rinsed (for example, in 2X SSC/0.3% SDS) and then washed with an appropriate wash solution and with gentle agitation. The stringency desired will be a reflection of the conditions under which the membrane (filter) is washed.

Specifically, the stringency of a given reaction (i.e., the degree of homology necessary for successful hybridization) will depend on the washing conditions to which the filter from the Southern Blot is subjected after hybridization. "Low-stringency" conditions as defined herein will comprise washing a filter from a Southern Blot with a solution of 0.2X SSC/0.1% SDS at 20° C. for 15 minutes. "Standard-stringency" conditions comprise a further washing step comprising washing the filter from the Southern Blot a second time with a solution of 0.2X SSC/0.1% SDS at 37° C. for 30 minutes.

The present invention also discloses a process for the production of the cellulase. It is possible to produce the cellulase by screening soda lake samples to produce and isolating the appropriate cellulase producing organism. That organism can then be grown up according to art recognized means for growing such Actinomycetes. However, rather than isolating the correct cellulase producing strain, it is far simpler and more efficient to isolate the cellulase according to the present invention utilizing genetic engineering techniques by transforming a suitable host cell with DNA provided herein which encodes the cellulase and cultivating the resultant recombinant microorganism under conditions appropriate for host cell growth and cellulase expression. As a first step, the chromosomal DNA may be obtained from the donor Actinomycete strain by, for example, the method of Saito and Miura (Saito & Miura, *Biochim. Biophys. Acta.*, Vol. 72, pp. 619 (1963)) or by a similar method. Restriction enzyme cleavage of the chromosomal DNA thus obtained gives DNA fragments containing the alkaline cellulase gene. For this purpose, any restriction enzyme may be used provided that it does not cleave the region of said gene. In the alternative, a restriction enzyme may be used which cleaves the gene, using however, a reduced enzyme concentration or incubation time to permit only partial digestion. A preferred restriction endonuclease is Sau3A. From the resulting digestion mixture, suitable fragments (4–10 kb) may be isolated and used to transform a suitable host cell with a DNA construct.

The gene encoding the cellulase of the present invention can be cloned using λ-phage (expression) vectors and *E. coli* host cells. (Alternatively PCR cloning using consensus primers designed on conserved domains may be used). Applicants have discovered that transformation of the gene encoding the cellulase of the present invention and expression in *E. Coli* results in an active protein. After a first cloning step in *E. coli*, a cellulase gene according to the present invention can be transferred to a more preferred industrial expression host such as Bacillus or Streptomyces species, a filamentous fungus such as Aspergillus or Trichoderma, or a yeast such as Saccharomyces. High level expression and secretion obtainable in these host organisms allows accumulation of the cellulase in the fermentation medium from which it can subsequently be recovered.

The cellulase may be recovered from the medium by conventional procedures including separating the cells from the medium by centrifugation or filtration, if necessary after disruption of the cells, precipitating the proteinaceous components of the supernatant or filtrate by means of a salt, e.g., ammonium sulfate, followed by purification by a variety of chromatographic procedures, e.g., ion exchange chromatography, affinity chromatography or similar art recognized procedures. For the production of the alkaline cellulase according to the invention, it is preferred to cultivate under alkaline conditions using media containing a cellulose based energy source.

Preferably, the expression host cell comprises a Bacillus spp., more preferably *Bacillus licheniformis* or *Bacillus subtilis*. In an especially preferred embodiment, the transformation host is deleted for protease genes to ensure that the product cellulase is not subject to proteolysis in the fermentation broth or concentrates thereof. A preferred general transformation and expression protocol for protease deleted Bacillus strains is provided in Ferrari et al., U.S. Pat. No. 5,264,366, incorporated herein by reference. Transformation and expression in Aspergillus is described in, for example, Berka et al., U.S. Pat. No. 5,364,770, incorporated herein by reference. Applicants have found that transformation of the instant gene into Bacillus was poor or ineffective in terms of resulting expression when the native regulatory machinery was utilized. Accordingly, when transforming into Bacillus spp., it is preferred to utilize the aprE promoter in combination with standard known Bacillus derived signal and other regulatory sequences. When the transformation host cell is Aspergillus the preferred promoter is glaA.

Treatment of textiles according to the present invention contemplates textile processing or cleaning with a composition comprising a cellulase. Such treating includes, but is not limited to, stonewashing, modifying the texture, feel and/or appearance of cellulose containing fabrics or other techniques used during manufacturing or cleaning/reconditioning of cellulose containing fabrics. Additionally, treating within the context of this invention contemplates the removal of "immature" or "dead" cotton, from cellulosic fabric or fibers. Immature cotton is significantly more amorphous than mature cotton and results in a lesser quality fabric when present due to, for example, uneven dyeing. The composition contemplated in the present invention further includes an enlarged cellulase component for use in washing of a soiled manufactured cellulose containing fabric. For example, the enlarged cellulase may be used in a detergent composition for washing laundry. Detergent compositions useful in accordance with the present invention include special formulations such as pre-wash, pre-soak and home-use color restoration compositions. Such treating compositions, as described herein, may be in the form of a concentrate which requires dilution or in the form of a dilute solution or form which can be applied directly to the cellulose containing fabric. General treatment techniques for cellulase treatment of textiles are described in, for example, EP Publication No. 220 016 and GB Application Nos. 1,368,599 and 2,095,275.

Treatment of a cellulosic material according to the present invention further contemplates the treatment of animal feed, pulp and/or paper, food and grain for purposes known in the art. For example, cellulase is known to increase the value of animal feed, improve the drainability of wood pulp, enhance food products and reduce fiber in grain during the grain wet milling process or dry milling process.

Treating according to the instant invention comprises preparing an aqueous solution which contains an effective amount of cellulase together with other optional ingredients including, for example, a buffer, a surfactant, and/or a scouring agent. An effective amount of cellulase enzyme composition is a concentration of cellulase enzyme sufficient for its intended purpose. Thus, for example, an "effective amount" of cellulase in a stonewashing composition according to the present invention is that amount which will provide the desired effect, e.g., to produce a worn and faded look in the seams and on fabric panels. Similarly, an "effective amount" of cellulase in a composition intended for improving the feel and/or appearance of a cellulose containing fabric is that amount which will produce measurable improvements in the feel, e.g., improving the smoothness of the fabric, or appearance, e.g., removing pills and fibrils which tend to reduce the sharpness in appearance of a fabric. The amount of cellulase employed is also dependent on the equipment employed, the process parameters employed (the temperature of the cellulase treatment solution, the exposure time to the cellulase solution, and the like), and the cellulase activity (e.g., a particular solution will require a lower concentration of cellulase where a more active cellulase composition is used as compared to a less active cellulase composition). The exact concentration of cellulase in the aqueous treatment solution to which the fabric to be treated is added can be readily determined by the skilled artisan based on the above factors as well as the desired result. In stonewashing processes, it has generally been preferred that the cellulase be present in the aqueous treating solution in a concentration of from about 0.5 to 5,000 ppm and most preferably about 10 to 200 ppm total protein. In compositions for the improvement of feel and/or appearance of a cellulose containing fabric, it has generally been preferred that the cellulase be present in the aqueous treating solution in a concentration of from about 0.1 to 2000 ppm and most preferably about 0.5 to 200 ppm total protein.

In a preferred treating embodiment, a buffer is employed in the treating composition such that the concentration of buffer is sufficient to maintain the pH of the solution within the range wherein the employed cellulase exhibits activity which, in turn, depends on the nature of the cellulase employed. The exact concentration of buffer employed will depend on several factors which the skilled artisan can readily take into account. For example, in a preferred embodiment, the buffer as well as the buffer concentration are selected so as to maintain the pH of the final cellulase solution within the pH range required for optimal cellulase activity. The determination of the optimal pH range of the enlarged cellulases of the invention can be ascertained according to well known techniques. Suitable buffers at pH within the activity range of the enlarged cellulase are well known to those skilled in the art in the field.

In addition to cellulase and a buffer, the treating composition may optionally contain a surfactant. Suitable surfactants include any surfactant compatible with the cellulase and the fabric including, for example, anionic, non-ionic and ampholytic surfactants. Suitable anionic surfactants for use herein include linear or branched alkylbenzenesulfonates; alkyl or alkenyl ether sulfates having linear or branched alkyl groups or alkenyl groups; alkyl or alkenyl sulfates; olefinsulfonates; alkanesulfonates and the like. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3. Ampholytic surfactants include quaternary ammonium salt sulfonates, and betaine-type ampholytic surfactants. Such ampholytic surfactants have both the positive and negative charged groups in the same molecule. Nonionic surfactants generally comprise polyoxyalkylene ethers, as well as higher fatty acid alkanolamides or alkylene oxide adduct thereof, and fatty acid glycerine monoesters. Mixtures of surfactants can also be employed in manners known to those skilled in the art.

A concentrated cellulase composition can be prepared for use in the methods described herein. Such concentrates contain concentrated amounts of the cellulase composition described above, buffer and surfactant, preferably in an aqueous solution. When so formulated, the cellulase concentrate can readily be diluted with water so as to quickly and accurately prepare enlarged cellulase preparations having the requisite concentration of each constituent. When aqueous concentrates are formulated, these concentrates can be diluted so as to arrive at the requisite concentration of the components in the cellulase solution as indicated above. As is readily apparent, such cellulase concentrates will permit facile formulation of the cellulase solutions as well as permit feasible transportation of the composition to the location where it will be used. The treating concentrate can be in any art recognized form, for example, liquid, emulsion, gel, or paste. Such forms are well known to those skilled in the art.

When a solid cellulase concentrate is employed, the cellulase composition may be a granule, a powder, an agglomerate or a solid disk. The granules can be formulated so as to contain materials to reduce the rate of dissolution of the granules into the wash medium. Such materials and granules are disclosed in U.S. Pat. No. 5,254,283 which is incorporated herein by reference in its entirety.

Other materials can also be used with or placed in the cellulose composition of the present invention as desired, including stones, pumice, fillers, solvents, enzyme activators, and anti-redeposition agents depending on the eventual use of the composition.

By way of example, stonewashing methods will be described in detail, however, the parameters described are readily modified by the skilled artisan for other applications, i.e., improving the feel and/or appearance of a fabric. The cellulose containing fabric is contacted with the cellulase containing stonewashing composition containing an effective amount of the cellulase by intermingling the treating composition with the stonewashing composition, and thus bringing the cellulase enzyme into proximity with the fabric. Subsequently, the aqueous solution containing the cellulase and the fabric is agitated. If the treating composition is an aqueous solution, the fabric may be directly soaked in the solution. Similarly, where the stonewashing composition is a concentrate, the concentrate is diluted into a water bath with the cellulose containing fabric. When the stonewashing composition is in a solid form, for example a pre-wash gel or solid stick, the stonewashing composition may be contacted by directly applying the composition to the fabric or to the wash liquor.

The cellulose containing fabric is incubated with the stonewashing solution under conditions effective to allow the enzymatic action to confer a stonewashed appearance to the cellulose containing fabric. For example, during stonewashing, the pH, liquor ratio, temperature and reaction time may be adjusted to optimize the conditions under which the stonewashing composition acts. "Effective conditions" necessarily refers to the pH, liquor ratio, and temperature which allow the cellulase enzyme to react efficiently with cellulose containing fabric, in this case to produce the stonewashed effect. Generally, the cellulases of the present invention should be utilized under conditions operable for the use of the parent cellulase(s). However, such conditions are readily ascertainable by one of skill in the art. The reaction conditions effective for the stonewashing compositions of the present invention are substantially similar to well known methods used with corresponding prior art cellulase compositions. Accordingly, it is within the skill of those in the art to maximize conditions for using the stonewashing compositions according to the present invention.

The liquor ratios during stonewashing, i.e., the ratio of weight of stonewashing composition solution (i.e., the wash liquor) to the weight of fabric, employed herein is generally an amount sufficient to achieve the desired stonewashing effect in the denim fabric and is dependent upon the process used. Preferably, the liquor ratios are from about 4:1 to about 50:1; more preferably from about 5:1 to about 20:1, and most preferably from about 10:1 to about 15:1.

Reaction temperatures during stonewashing with the present stonewashing compositions are governed by two competing factors. Firstly, higher temperatures generally correspond to enhanced reaction kinetics, i.e., faster reactions, which permit reduced reaction times as compared to reaction times required at lower temperatures. Accordingly, reaction temperatures are generally at least about 10° C. and greater. Secondly, cellulase is a protein which loses activity beyond a given reaction temperature, which temperature is dependent on the nature of the cellulase used. Thus, if the reaction temperature is permitted to go too high, the cellulolytic activity is lost as a result of the denaturing of the cellulase. While standard temperatures for cellulase usage in the art are generally in the range of 35° C. to 65° C., which conditions would also be expected to be suitable for the cellulase of the invention, the optimal temperature conditions should be ascertained according to well known techniques with respect to the specific cellulase used.

Reaction times are dependent on the specific conditions under which the stonewashing occurs. For example, pH, temperature and concentration of cellulase will all effect the optimal reaction time. Generally, reaction times are from about 5 minutes to about 5 hours, and preferably from about 10 minutes to about 3 hours and, more preferably, from about 20 minutes to about 1 hour.

According to yet another preferred embodiment of the present invention, the cellulase of the invention may be employed in a detergent composition. The detergent compositions according to the present invention are useful as pre-wash compositions, pre-soak compositions, or for cleaning during the regular wash or rinse cycle. Preferably, the detergent composition of the present invention comprises an effective amount of cellulase, a surfactant, and optionally includes other ingredients described below.

An effective amount of cellulase employed in the detergent compositions of this invention is an amount sufficient to impart the desirable effects known to be produced by cellulase on cellulose containing fabrics, for example, depilling, softening, anti-pilling, surface fiber removal, anti-graying and cleaning. Preferably, the cellulase in the detergent composition is employed in a concentration of from about 10 ppm to about 20,000 ppm of detergent.

The concentration of cellulase enzyme employed in the detergent composition is preferably selected so that upon dilution into a wash medium, the concentration of cellulase enzyme is in a range of about 0.01 to about 1000 ppm, preferably from about 0.02 ppm to about 500 ppm, and most preferably from about 0.5 ppm to about 250 ppm total protein. The amount of cellulase enzyme employed in the detergent composition will depend on the extent to which the detergent will be diluted upon addition to water so as to form a wash solution.

The detergent compositions of the present invention may be in any art recognized form, for example, as a liquid, in granules, in emulsions, in gels, or in pastes. Such forms are well known to the skilled artisan. When a solid detergent composition is employed, the cellulase is preferably formulated as granules. Preferably, the granules can be formulated so as to additionally contain a cellulase protecting agent. The granule can be formulated so as to contain materials to reduce the rate of dissolution of the granule into the wash medium. Such materials and granules are disclosed in U.S. Pat. No. 5,254,283 which is incorporated herein by reference in its entirety.

The detergent compositions of this invention employ a surface active agent, i.e., surfactant, including anionic, non-ionic and ampholytic surfactants well known for their use in detergent compositions.

Suitable anionic surfactants for use in the detergent composition of this invention include linear or branched alkyl-benzenesulfonates; alkyl or alkenyl ether sulfates having linear or branched alkyl groups or alkenyl groups; alkyl or alkenyl sulfates; olefinsulfonates; and alkanesul-fonates. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3. Ampholytic surfactants include quaternary ammonium salt sulfonates, and betaine-type ampholytic surfactants. Such ampholytic surfactants have both the positive and negative charged groups in the same molecule. Nonionic surfactants generally comprise polyoxyal-kylene ethers, as well as higher fatty acid alkanolamides or alkylene oxide adduct thereof, fatty acid glycerine monoesters, and the like. Suitable surfactants for use in this invention are disclosed in British Patent Application No. 2 094 826 A, the disclosure of which is incorporated herein by reference. Mixtures of such surfactants can also be used. The surfactant or a mixture of surfactants is generally employed in the detergent compositions of this invention in an amount from about 1 weight percent to about 95 weight percent of the total detergent composition and preferably from about 5 weight percent to about 45 weight percent of the total detergent composition. In addition to the cellulase composition and the surfactant(s), the detergent compositions of this invention can optionally contain one or more of the following components:

Hydrolases Except Cellulase

Suitable hydrolases include carboxylate ester hydrolase, thioester hydrolase, phosphate monoester hydrolase, and phosphate diester hydrolase which act on the ester bond; glycoside hydrolase which acts on glycosyl compounds; an enzyme that hydrolyzes N-glycosyl compounds; thioether hydrolase which acts on the ether bond; and a-amino-acyl-peptide hydrolase, peptidyl-amino acid hydrolase, acyl-amino acid hydrolase, dipeptide hydrolase, and peptidyl-peptide hydrolase which act on the peptide bond. Preferable among them are carboxylate ester hydrolase, glycoside hydrolase, and peptidyl-peptide hydrolase. Suitable hydrolases include (1) proteases belonging to peptidyl-peptide hydrolase such as pepsin, pepsin B, rennin, trypsin, chymotrypsin A, chymotrypsin B, elastase, enterokinase, cathepsin C, papain, chymopapain, ficin, thrombin, fibrinolysin, renin, subtilisin, aspergillopeptidase A, collagenase, clostridiopeptidase B, kallikrein, gastrisin, cathepsin D., bromelin, keratinase, chymotrypsin C, pepsin C, aspergillopeptidase B, urokinase, carboxypeptidase A and B, and aminopeptidase; (2) glycoside hydrolases (cellulase which is an essential ingredient is excluded from this group) α-amylase, β-amylase, gluco amylase, invertase, lysozyme, pectinase, chitinase, and dextranase. Preferably among them are α-amylase and β-amylase. They function in acid to neutral systems, but one which is obtained from bacteria exhibits high activity in an alkaline system; (3) carboxylate ester hydrolase including carboxyl esterase, lipase, pectin esterase, and chlorophyllase. Especially effective among them is lipase.

The hydrolase other than cellulase is incorporated into the detergent composition as much as required according to the purpose. It should preferably be incorporated in an amount of 0.001 to 5 weight percent, and more preferably 0.02 to 3 weight percent, in terms of purified protein. This enzyme should be used in the form of granules made of crude enzyme alone or in combination with other components in the detergent composition. Granules of crude enzyme are used in such an amount that the purified enzyme is 0.001 to 50 weight percent in the granules. The granules are used in an amount of 0.002 to 20 and preferably 0.1 to 10 weight percent. As with cellulases, these granules can be formulated so as to contain an enzyme protecting agent and a dissolution retardant material.

Cationic Surfactants and Long-Chain Fatty Acid Salts

Such cationic surfactants and long-chain fatty acid salts include saturated or unsaturated fatty acid salts, alkyl or alkenyl ether carboxylic acid salts, a-sulfofatty acid salts or esters, amino acid-type surfactants, phosphate ester surfactants, quaternary ammonium salts including those having 3 to 4 alkyl substituents and up to 1 phenyl substituted alkyl substituents. Suitable cationic surfactants and long-chain fatty acid salts are disclosed in British Patent Application No. 2 094 826 A, the disclosure of which is incorporated herein by reference. The composition may contain from about 1 to about 20 weight percent of such cationic surfactants and long-chain fatty acid salts.

Builders

A. Divalent sequestering agents

The composition may contain from about 0 to about 50 weight percent of one or more builder components selected from the group consisting of alkali metal salts and alkanolamine salts of the following compounds: phosphates, phosphonates, phosphonocarboxylates, salts of amino acids, aminopolyacetates high molecular electrolytes, non-dissociating polymers, salts of dicarboxylic acids, and aluminosilicate salts. Suitable divalent sequestering gents are disclosed in British Patent Application No. 2 094 826 A, the disclosure of which is incorporated herein by reference.

B. Alkalis or inorganic electrolytes

The composition may contain from about 1 to about 50 weight percent, preferably from about 5 to about 30 weight percent, based on the composition of one or more alkali metal salts of the following compounds as the alkalis or inorganic electrolytes: silicates, carbonates and sulfates as well as organic alkalis such as triethanolamine, diethanolamine, monoethanolamine and triisopropanolamine.

Antiredeposition Agents

The composition may contain from about 0.1 to about 5 weight percent of one or more of the following compounds as antiredeposition agents: polyethylene glycol, polyvinyl alcohol, polyvinylpyrrolidone and carboxymethylcellulose.

Among them, a combination of carboxymethyl-cellulose and/or polyethylene glycol with the cellulase composition of the present invention provides for an especially useful dirt removing composition.

Bleaching Agents

The use of the cellulase of the present invention in combination with a bleaching agent such as potassium monopersulfate, sodium percarbonate, sodium perborate, sodium sulfate/hydrogen peroxide adduct and sodium chloride/hydrogen peroxide adduct or/and a photo-sensitive bleaching dye such as zinc or aluminum salt of sulfonated phthalocyanine further improves the detergenting effects. Similarly, bleaching agents and bleach catalysts as described in EP 684 304 may be used.

Bluing Agents and Fluorescent Dyes

Various bluing agents and fluorescent dyes may be incorporated in the composition, if necessary. Suitable bluing agents and fluorescent dyes are disclosed in British Patent Application No. 2 094 826 A, the disclosure of which is incorporated herein by reference.

Caking Inhibitors

The following caking inhibitors may be incorporated in the powdery detergent: p-toluenesulfonic acid salts, xylenesulfonic acid salts, acetic acid salts, sulfosuccinic acid salts, talc, finely pulverized silica, amorphous silicas, clay, calcium silicate (such as Micro-Cell of Johns Manville Co.), calcium carbonate and magnesium oxide.

Cellulase-Activators

The activators vary depending on variety of the cellulases. In the presence of proteins, cobalt and its salts, magnesium and its salts, and calcium and its salts, potassium and its salts, sodium and its salts or monosaccharides such as mannose and xylose, the cellulases are activated and their deterging powers are improved remarkably.

Antioxidants

The antioxidants include, for example, tert-butylhydroxytoluene, 4,4'-butylidenebis(6-tert-butyl-3-methylphenol), 2,2'-butylidenebis(6-tert-butyl4- methylphenol), monostyrenated cresol, distyrenated cresol, monostyrenated phenol, distyrenated phenol and 1,1-bis(4-hydroxy-phenyl)cyclohexane.

Solubilizers

The solubilizers include, for example, lower alcohols such as ethanol, benzenesulfonate salts, lower alkylbenzene-sulfonate salts such as p-toluenesulfonate salts, glycols such as propylene glycol, acetylbenzene-sulfonate salts, acetamides, pyridinedicarboxylic acid amides, benzoate salts and urea.

The detergent composition of the present invention can be used in a broad pH range from acidic to alkaline pH. In a preferred embodiment, the detergent composition of the present invention can be used in mildly acidic, neutral or alkaline detergent wash media having a pH of from above 5 to no more than about 12.

Aside from the above ingredients, perfumes, buffers, preservatives, dyes and the like can be used, if desired, with the detergent compositions of this invention. Such components are conventionally employed in amounts heretofore used in the art.

When a detergent base used in the present invention is in the form of a powder, it may be one which is prepared by any known preparation methods including a spray-drying method and a granulation method. The detergent base obtained particularly by the spray-drying method, agglomeration method, dry mixing method or non-tower route methods are preferred. The detergent base obtained by the spray-drying method is not restricted with respect to preparation conditions. The detergent base obtained by the spray-drying method is hollow granules which are obtained by spraying an aqueous slurry of heat-resistant ingredients, such as surface active agents and builders, into a hot space. After the spray-drying, perfumes, enzymes, bleaching agents, inorganic alkaline builders may be added. With a highly dense, granular detergent base obtained such as by the spray-drying-granulation or agglomeration method, various ingredients may also be added after the preparation of the base.

When the detergent base is a liquid, it may be either a homogeneous solution or an inhomogeneous dispersion. For removing the decomposition of carboxymethylcellulose by the cellulase in the detergent, it is desirable that carboxymethylcellulose is granulated or coated before the incorporation in the composition.

The detergent compositions of this invention may be incubated with cellulose containing fabric, for example soiled fabrics, in industrial and household uses at temperatures, reaction times and liquor ratios conventionally employed in these environments. The incubation conditions, i.e., the conditions effective for treating cellulose containing fabrics with detergent compositions according to the present invention, will be readily ascertainable by those of skill in the art. Accordingly, the appropriate conditions effective for treatment with the present detergents will correspond to those using similar detergent compositions which include known cellulases.

Detergents according to the present invention may additionally be formulated as a pre-wash in the appropriate solution at an intermediate pH where sufficient activity exists to provide desired improvements softening, depilling, pilling prevention, surface fiber removal or cleaning. When the detergent composition is a pre-soak (e.g., pre-wash or pre-treatment) composition, either as a liquid, spray, gel or paste composition, the enlarged cellulase enzyme is generally employed from about 0.0001 to about 1 weight percent based on the total weight of the pre-soak or pre-treatment composition. In such compositions, a surfactant may optionally be employed and when employed, is generally present at a concentration of from about 0.005 to about 20 weight percent based on the total weight of the pre-soak. The remainder of the composition comprises conventional components used in the pre-soak, i.e., diluent, buffers, other enzymes (proteases), and the like at their conventional concentrations.

It is contemplated that compositions comprising truncated cellulase enzymes described herein can be used in home use as a stand alone composition suitable for restoring color to faded fabrics (see, for example, U.S. Pat. No. 4,738,682, which is incorporated herein by reference in its entirety) as well as used in a spot-remover and for depilling and antipilling (pilling prevention).

The use of the cellulase according to the invention may be particularly effective in feed additives and in the processing of pulp and paper. These additional industrial applications are described in, for example, PCT Publication No. 95/16360 and Finnish Granted Patent No. 87372, respectively.

In order to further illustrate the present invention and advantages thereof, the following specific examples are given with the understanding that they are being offered to illustrate the present invention and should not be construed in any way as limiting its scope.

EXAMPLES

Example 1

Isolation of Cellulase Producing Micro-organisms from Alkaline Soil and Water Samples Alkaline mud samples were suspended in 5 ml 4% (w/v) NaCl: 1 % (w/v) $Na_2CO_3$ and shaken vigorously. Serial dilutions in the same solution were plated out on Soil Extract Agar, pH 10 containing rifampicine 50 $\mu g$ $ml^{-1}$.

Soil Extract Agar was prepared as follows: 1 kg of garden soil is suspended in 1 liter of demineralised water. The suspension is autoclaved for 20 minutes at 120° C. The suspension is filtered over a glass fiber filter (Whatman, GF/A) and the solids washed twice with demineralised water (1×200 ml, 1×100 ml). The filtrate is made up to 1 liter with water. An equal volume of sterilized filtrate is mixed with a sterile solution of 8% (w/v) NaCl: 2% (w/v) $Na_2CO_3$ with 2% (w/v) agar added for solidification.

The plates were incubated at 30° C. for several weeks in a closed box to prevent evaporation. The plates were examined periodically under the stereo-microscope and micro-colonies were transferred to Alkaline Agar containing 0.3% (w/v) carboxymethylcellulose. Duplicate cultures were used to detect cellulase activity by flooding one of the plates with 0.1% (w/v) Congo Red for 15 minutes. The plates were destained with 1 M NaCl for 30 minutes. The strains that showed a clearing zone around the colony were selected as potential cellulase producing microorganisms.

Strains that showed clearing zones were fermented in 25 ml as described in PCT publication No. WO 96/34108 (page 8) after which CMC was added.

Using the method described above, the strain producing the cellulase of the invention was isolated and further characterized as filamentous bacteria. Based on appearance and partial 16s rRNA gene sequence analysis (Example 4), the microorganism is classified as a species of Streptomyces.

A morphological examination of the cellulase producing strain was made. When grown on Soil Extract Agar at pH 10;

the initially small round glistening transparent colony developed after a few days a white to gray-white aerial mycelium. On Alkaline Agar the strain forms a dry leathery, cream colored, opaque colony producing aerial mycelium on maturity. Under the microscope the strain exhibits extensively branched pseudo-mycelium which fragments into irregular rods, isolated spores and spores in chains.

Example 2

Isolation of DNA, Transformation and Expression of Cellulase

An alkaliphilic Actinomycete strain isolated per Example 1 was chosen as a donor strain for expression cloning in E. coli. Chromosomal DNA was isolated according to the method described by Saito & Miura, Biochim. Biophys. Acta., Vol. 72, pp. 619–629 (1963).

The isolated chromosomal DNA is partially digested by the restriction enzyme Sau3A using serial diluted enzyme solutions, for one hour at 37° C. using React Buffers (Gibco BRL Life Technologies, Gaithersburg, Md., USA) under conditions recommended by the supplier. The digested DNA is fractionated by agarose gel electrophoresis and suitable fractions (2–6 kb) are isolated from the gel using QIAquick Gel Extraction Kit according to the protocol described by the supplier (QIAGEN Inc., Chatsworth, Calif., USA).

Genomic gene libraries of the alkalitolerant Actinomycete strains are constructed in a pUC19-derived plasmid (Yanisch-Perron, C. et al., (1985) Gene 33:103). Recombinant clones are screened by agar diffusion as described by Wood et al., Meth. Enzym., Vol. 160, pp. 59–74 (1988). Strains that show clearing zones around the colony are isolated. Plasmid DNA of the cellulase producing recombinant is isolated using a QIAprep Plasmid Kit according to the protocol described by the supplier (QIAGEN Inc.). The nucleotide sequence of a fragment of 4.5 kb is determined from both ends until a sequence bearing resemblance to known conserved cellulase sequences was identified by a FastA search against the public data bases. Upon determination of conserved sequences, the remainder of the gene was sequenced.

The isolated gene contains 1056 base pairs coding for a precursor protein having 371 amino acids including a signal sequence of 39 amino acids. The mature protein is comprised of 344 amino acids and a deduced molecular weight of 34,902 and pI of 4.5. The nucleotide sequence of the gene (SEQ. ID. NO:2) coding for said cellulase and the deduced amino acid sequence (SEQ ID NO:1) of the mature cellulase are illustrated in FIGS. 1 and 2.

The DNA fragment of the cellulase gene coding for the structural gene prepared as described above was cloned in the vector pHPLT (see FIG. 4). This vector contains the promoter and signal sequence of the thermostable amylase gene of Bacillus licheniformis and causes high expression in Bacillus (see FIG. 5). Transformation of competent Bacillus host cells was performed with resulting recombinant cellulase producing Bacillus clones isolated and grown under suitable conditions for producing the cloned cellulase.

Example 3

Purification of Cellulase

The cellulase producing Bacillus licheniformis clones from Example 2 were grown in a complex medium comprising Trypton Soya Broth (Oxoid CM129) 3%, 20 μg/ml neomycin. Purification may be accomplished as follows:

Fermentation broth is separated from the culture liquid by centrifugation (8000 rpm). The cellulase in the supernatant is precipitated with ammonium sulphate (65% saturation). The precipitate is dissolved in 25 mM phosphate buffer pH 7+5 mM EDTA until a conductivity of 7 mS/cm was achieved. This solution is applied to a Q-Sepharose FF (diameter 5 cm, length 10 cm) Anion Exchange column, after which the column is washed with 25 mM phosphate buffer pH 7+5 mM EDTA until an absorbency of 0.2 AU. A gradient of 0 to 0.5 M NaCl in 25 mM phosphate pH 7 is applied to the column in 80 minutes followed by a gradient from 0.5 to 1 M NaCl in 10 minutes. Elution may be performed in the first gradient. After elution the column is cleaned (upflow) with 1 M NaOH and equilibrated again with 25 mM phosphate pH 7+5 mM EDTA.

Example 4

Characterization of 16S rDNA from Cellulase Producing Actinomycete

The nucleotide sequence of the first 400 bps of the 16S-rDNA sequence of the donor organism isolated in Example 1 which produces the cellulase of Examples 2 and 3 was obtained and is provided in FIG. 6 (SEQ.ID.NO:3). This sequence was analyzed with the FastA sequence analysis software package to provide a comparison with the sequences in public databases. The analysis results illustrated that the nearest neighbor was Streptomyces albus which had a 16S rDNA identity of 97.6% in an overlap of 422 base pairs. The percentage of identity of the partial 16S rDNA fraction of the strains is a strong indication that the strain represents an unknown species of Actinomycetes. Based on an analysis of the obtained 16S rRNA sequence (in combination with the appearance, Example 1), the microorganism was classified as a species of Streptomyces.

Example 5

Properties of the Cellulase According to the Invention

To determine the pH/temperature profile of the approximately 35 kD cellulase according to the invention, the activity of the cellulase was measured on CMC at various pH and temperature values. This procedure was colorimetric method for the determination of (total) cellulase activity, utilizing Carboxy Methyl Cellulose (CMC) as substrate. Cellulase liberates reducing sugars, which react with "PAH-BAH" at high pH and temperature. This reaction product can be measured with a spectrophotometer. The activity was determined using a calibration curve of glucose.

Chemicals: CMC, low viscosity (Sigma C-5678, batch # 23HO244)

Hydroxybenzoic acidhydrazide ("PAHBAH",Sigma H-9882)

D-glucose monohydrate (Boom 8342)

$NaH_2PO_4*1$ aq (Merck 6346)

$H_3PO_4$ (85%; Merck 573)

Citric acid*1 aq (Merck 244)

4 N NaOH 0.5 N HCl

Incubation buffer A (0.01 M phosphate):

1.38 g $NaH_2PO_4*1$ aq was dissolved in 800 ml of demineralized (demi) water. The pH was adjusted to 7 with 4 N NaOH and the mixture was filled up to 1000 ml with demi water. Finally the pH was checked and adjusted if necessary. This buffer was used for dissolving and diluting the enzyme samples.

Incubation buffer B (0.1 M citrate +0.1 M phosphate):

23.06 g H3PO4 was dissolved in demi water to a final volume of 200 ml (=1 M). 42 g citric acid was dissolved in demi water to a final volume of 200 ml (=1 M). 20 ml citric acid solution was combined with 20 ml phosphoric acid, after which the volume was filled up to 150 ml with demi water. The pH (range from 4 to 10) was adjusted with 4 N NaOH and the final volume filled up to 200 ml with demi water. This buffer was used for diluting the substrate preparation.

Incubation buffer C (0.05 M citrate+0.05 M phosphate):

Incubation buffer B was diluted 1:1 with demi water. The pH was checked and corrected if necessary. This solution was used for the glucose calibration curve.

Substrate preparation (1%):

Under strong stirring 1 g of CMC was slowly added to 100 ml of demi water. Vigorously stirring was continued for at least one hour followed by a treatment with an ultraturrax during 30 seconds.

Enzyme solution:

The enzyme sample was dissolved and diluted in incubation buffer A to an activity of about 0.05 U/ml (half-way the glucose calibration curve).

Colour reagent (5%):

9 PAHBAH was dissolved in 80 ml of 0.5 N HCl, after which the solution was filled up to 100 ml with 0.5 N HCl. Prior to use, one part of the PAHBAH solution was diluted with four parts of 0.5 N NaOH.

Calibration curve:

Stock solution #1: 1000 mg glucose was dissolved in 100 ml demi water (10 mg/ml).

Stock solution #2: 0.5 ml stock solution #1 was diluted with 9.5 ml incubation buffer C of the pH concerned (0.5 mg/ml).

The following titration scheme was used:

| $\mu$Mol glucose/0.1 ml | stock solution #2 | incubation buffer C |
|---|---|---|
| 0 | 0 $\mu$l | 1000 $\mu$l |
| 0.05 | 200 $\mu$l | 800 $\mu$l |
| 0.1 | 400 $\mu$l | 600 $\mu$l |
| 0.15 | 600 $\mu$l | 400 $\mu$l |
| 0.2 | 800 $\mu$l | 200 $\mu$l |
| 0.25 | 1000 $\mu$l | 0 $\mu$l |

Assay procedure:
(1) test tubes of the glucose standards, controls, samples and blanks were filled with 0.5 ml of substrate (1%) and 0.5 ml incubation buffer B of desired pH and placed in a waterbath of the desired temperature;
(2) the solutions were pre-incubated for 10 minutes;
(3) every 15 seconds 100 $\mu$l glucose standard, control or sample was added to the tubes with substrate;
(4) the solutions were vortexed for 3 seconds and placed back in the waterbath;
(5) each sample was incubated for 30 minutes;
(6) the enzyme reaction was stopped by adding 3 ml of the PAHBAH reagent;
(7) the resulting solutions were vortexed for 3 seconds and placed in a rack outside the waterbath;
(8) when all tubes were stopped, 100 $\mu$l of sample was added to the blank tubes concerned and vortex 3 seconds;
(9) the samples were placed for 15 minutes in a boiling water bath;
(10) the resulting samples were cooled down in cold tap water for 5 to 10 minutes and then revortexed for 3 seconds;
(11) the absorbance of the mixture was measured at 410 nm with water as reference.

The results are shown in FIG. 3. As shown in FIG. 3, the pH optimum of the 35 kD cellulase is about 6 at 40° C. and 5 or less at 60° C.

---

What is claimed is:

1. A cellulase comprising the amino acid sequence provided in SEQ ID NO: 1 or a derivative thereof having cellulolytic activity and greater than 62% sequence identity to SEQ ID NO:1.

2. The cellulase according to claim 1 wherein said derivative has at least 75% sequence identity to SEQ ID NO: 1.

3. The cellulase according to claim 1, wherein said cellulase is encoded by a DNA sequence which is selected from the group consisting of DNA which corresponds in sequence to SEQ ID NO: 2 and DNA which has at least 76% sequence identity to SEQ ID NO: 2.

4. The cellulase according to claim 1, wherein said cellulase comprises the amino acid sequence provided in SEQ. ID. NO:1.

5. The cellulase according to claim 1, wherein said cellulase is obtained from an Actinomycete.

6. The cellulase according to claim 3, wherein said cellulase is encoded by the DNA sequence corresponding to SEQ ID NO:2.

7. The cellulase according to claim 3, wherein said cellulase is encoded by a DNA which has at least 90% sequence identity to SEQ ID NO: 2.

8. A detergent composition comprising the cellulase according to claim 1.

9. A detergent composition comprising the cellulase according to claim 3.

10. An animal feed additive comprising the cellulase according to claim 1.

11. A composition comprising the cellulase according to claim 1, wherein said composition is used for the treatment of textiles.

12. A composition comprising the cellulase according to claim 1, wherein said composition is used for the treatment of pulp and paper.

13. A cellulase obtained from an Actinomycete comprising the amino acid sequence provided in SEQ ID NO: 1 or an amino acid sequence having cellulolytic activity and greater than 62% sequence identity to the sequence provided in SEQ ID NO: 1.

14. A cellulase comprising the amino acid sequence provided in SEQ ID NO: 1 or a derivative thereof having cellulolytic activity and at least 90% sequence identity to SEQ ID NO: 1.

15. The cellulase according to claim 14, wherein said cellulase is obtained from Actinomycete.

16. The cellulase according to claim 14, wherein said cellulase is encoded by a DNA sequence which hybridizes to a second DNA molecule comprising at least a portion of the sequence according to SEQ ID NO: 2 under conditions of standard stringency.

* * * * *